US00PP17526P3

(12) United States Plant Patent
Meilland

(10) Patent No.: US PP17,526 P3
(45) Date of Patent: Mar. 27, 2007

(54) MINIATURE ROSE PLANT NAMED 'MEIVOUFAL'

(50) Latin Name: *Rosa hybrida*
Varietal Denomination: Meivoufal

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 194 days.

(21) Appl. No.: 10/844,340

(22) Filed: May 13, 2004

(65) Prior Publication Data

US 2004/0210972 P1 Oct. 21, 2004

Related U.S. Application Data

(63) Continuation of application No. 10/288,511, filed on Nov. 6, 2002, now abandoned, which is a continuation of application No. 09/573,162, filed on May 19, 2000, now abandoned.

(51) Int. Cl.
*A01H 5/00* (2006.01)

(52) U.S. Cl. ..... Plt./118
(58) Field of Classification Search ..... Plt./118
See application file for complete search history.

(56) References Cited

PUBLICATIONS

Canadian Ornamental Plant Foundation [online], [retrieved on Feb. 14, 2006]. Retrieved from the Internet <http://www.copf.org/plants_list.asp?LS=15&Page=2 &Breeder=Meilland%20International> one page.*

The Conard–Pyle Co. Sales Representatives [online], [retrieved on Feb. 14, 2006]. Retrieved from the Internet <http://www.conard–pyle.com/salesreplist.htm> one page.*

UPOV–ROM GTITM, Plant Variety Database, 2005/05, GTI Jouve Retrieval Software, Citation for *Rosa* 'Meivoufal'.*

* cited by examiner

*Primary Examiner*—Kent Bell
*Assistant Examiner*—June Hwu
(74) *Attorney, Agent, or Firm*—Buchanan, Ingersoll & Rooney PC

(57) ABSTRACT

A new and distinct variety of rose plant of the Miniature Class is provided which abundantly forms attractive double yellow blossoms of good color stability. The growth habit is low compact and bushy. Decorative dense dark green semi-glossy foliage is formed that contrasts nicely with the yellow blossoms.

1 Drawing Sheet

Botanical/commercial classification: *Rosa hybrida*/Miniature Rose Plant.
Varietal denomination: cv. Meivoufal.

SUMMARY OF THE INVENTION

The new variety of Miniature rose plant was created by artificial pollination wherein two parents were crossed which previously had been studied in the hope that they would contribute the desired characteristics. The female parent (i.e., the seed parent) of the new variety was the 'Savaje' variety (non-patented in the United States). The male parent (i.e., the pollen parent) was the product of the pollination of the 'Playboy' variety (non-patented in the United States) and the 'Lavglo' variety (U.S. Plant Pat. No. 7,136). The parentage of the new variety can be summarized as follows:

'Savaje'×('Playboy'×'Lavglo').

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) exhibits a low compact and bushy growth habit,
(b) forms in abundance attractive double yellow blossoms of good color stability, and
(c) forms decorative dense dark green semi-glossy foliage.

The bearing is very floriferous. The profusion of yellow blossoms contrast nicely with the dense dark green foliage.

The new variety of the present invention can be readily distinguished from its ancestors. For instance, the 'Savaje' variety forms larger flowers, the 'Playboy' variety forms flowers that are single to semi-double unlike the new variety, and the 'Lavglo' variety displays more petals per bloom. The flowers of the 'Poulgelb' variety (U.S. Plant Pat. No. 9,401) tend to be smaller and of a slightly lighter yellow coloration.

The new variety well meets the needs of the horticultural industry. It is particularly well-suited for pot forcing under greenhouse growing conditions to form an attractive gift plant.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety has been named the 'Meivoufal' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while growing on their own roots in greenhouses at LeCannet des Maures, Var, France. Dimensions in centimeters are shown at the bottom of the photograph.

FIG. 1—illustrates a specimen of a young shoot;

FIG. 2—illustrates specimens of two floral buds before the opening of the sepals;

FIG. 3—illustrates specimens of two floral buds at the opening of the sepals;

FIG. 4—illustrates specimens of two floral buds at the opening of the petals;

FIG. 5—illustrates a specimen of a flower during the course of opening;

Figures 1, 2, 3, 4, 5, 6, 7, 8, 9, 10, 11, 12, 13, 14, 15:
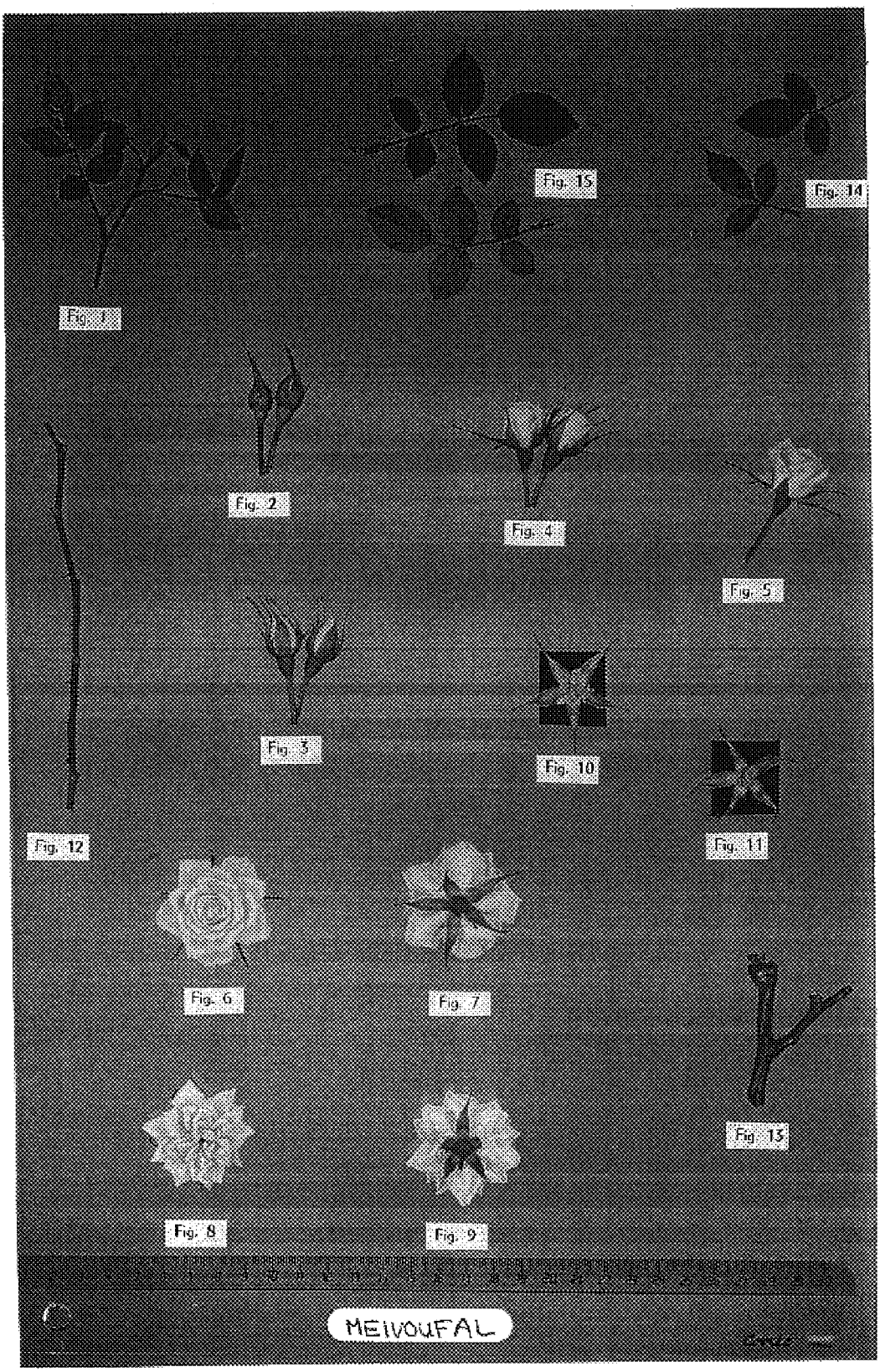
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of two leaves with three leaflets with the upper surface being shown at the top and the under surface being shown at the bottom; and FIG. 15—illustrates specimens of two leaves with five leaflets with the upper surface being shown at the top and the under surface being shown at the bottom.

DETAILED DESCRIPTION

The chart used in the identification of the colors is that of The Royal Horticultural Society (R.H.S. Colour Chart). The terminology which precedes reference to the chart has been added in some instances to indicate the corresponding colors in more common terms. The description is based on the observation of nine months old specimens of the new variety which were observed during March while growing on their own roots in greenhouses at LeCannet des Maures, Var, France.

Class: Dwarf Miniature.

Plant:

*Height.*—Approximately 20 to 25 cm. on average at the end of the growing season.

*Width.*—Approximately 30 to 35 cm. on average at the end of the growing season.

*Habit.*—Bushy.

Branches:

*Color.*—Young stems: near Green Group 143A with anthocyanin coloration near Greyed-Orange Group 176C. Adult wood: near Yellow-Green Group 146C.

*Texture.*—Young stems: smooth. Adult wood: Smooth.

*Thorns.*—Size: medium, and approximately 4 mm. in length on average. Quantity: very sparse as illustrated. Color: immature thorns are pale green, near Yellow-Green Group 145C suffused with Greyed-Red Group 182D, and mature thorns are near Yellow-Green Group 145C and only slightly suffused with Greyed-Red Group 182D. Configuration: fairly straight.

Leaves:

*Size.*—Approximately 8 cm. in length on average, and approximately 4.5 cm. in width on average.

*Petioles.*—Upper surface: non-glandular, and near Green Group 137A with light anthocyanin coloration near Greyed-Orange Group 176A. Under surface: pale green with numerous small prickles. Length: approximately 4 cm on average.

*Rachis.*—Possesses a smooth surface texture.

*Stipules.*—Adnate, pectinate, near Green Group 137C in coloration, approximately 6 mm. in length and approximately 2 mm. in width on average.

*Leaflets.*—Number: 3, 5 (most often), and 7. Shape: with an acute tip and an obtuse base (as illustrated). Size: the terminal leaflets are commonly approximately 3 to 3.2 cm. in length on average and approximately 2 cm. in width on average. Texture: smooth on the upper surface and bear prickles on the under surface of the leaf axil. Serration: minute and regular. General appearance: very dense, dark green and semi-glossy. Color (young foliage): Upper surface: near Green Group 137B. Under surface: near Green Group 137C. Color (adult foliage): Upper surface: dark green near Green Group 137A. Under surface: near Green Group 137D.

Inflorescence:

*Number of flowers.*—Commonly approximately 2 to 5 per stem.

*Peduncle.*—Short, without prickles, near Green Group 137C with anthocyanin coloration near Greyed-Orange Group 176A, and the length commonly is approximately 4 to 4.5 cm. on average.

*Sepals.*—Upper surface: tomentose, and near Green Group 138B. Under surface: glabrous and near Green Group 138A. Size: commonly approximately 2.5 cm. in length, and with extensions.

*Buds.*—Shape: conical. Size: medium for class, and approximately 1.5 cm. in length and approximately 1 cm. in diameter.

*Flower.*—Form: double and cup-shaped. Diameter: approximately 4.5 to 5 cm. on average when fully open. Color (when opening begins): Upper surface: near Yellow Group 12A. Under surface: near Yellow Group 12A. Color (when blooming): Upper surface: near Yellow Group 12A. Under surface: near Yellow Group 12A. Color (at end of opening): Upper surface: near Yellow Group 12A and 12B. Under surface: near Yellow Group 12A and 12B. Petal form: with reflexed edges. Petal shape: generally oval. Petal number: commonly approximately 43 to 45 on average. Petal size: the external petals commonly are approximately 2 cm. in length and approximately 2 cm. in width. Petal apex: pointed. Petal base: wedge-shaped. Petal texture: physically moderately firm. Petaloids: none observed to date. Basal spot on petals: none observed to date. Fragrance: none. Anthers: yellow, near Yellow Group 12B. Stamen number: approximately 68 on average. Filaments: approximately 0.4 cm. in length, and yellow, near Yellow Group 12B, in coloration. Pistil number: approximately 57 on average. Petal configuration: wedge-shaped. Pistil color: the stigma and style near Yellow-Green Group 145A and 145B. Stigmas: near Yellow-Green Group 145A and 145B. Styles: approximately 0.3 cm. in length on average, and near Yellow-Green Group 145A and 145B in coloration. Receptacle: smooth surface, medium green, near Green Group 138A, approximately 0.8 cm. in length and approximately 0.5 to 0.6 cm. in width on average, and in longitudinal section in the shape of a funnel. Lasting quality: approximately 10 days on average on the plant. Petal drop: good, the petals detach well.

Development:

*Vegetation.*—Strong.

*Blooming.*—Very abundant.

*Resistance to diseases.*—Good under greenhouse growing conditions with respect to Powdery Mildew.

*Propensity to form hips.*—None observed.

I claim:

1. A new and distinct variety of Miniature rose plant characterized by the following combination of characteristics:

(a) exhibits a low compact and bushy growth habit, (b) forms in abundance attractive double yellow blossoms of good color stability, and (c) forms decorative dense dark green semi-glossy foliage;

substantially as herein shown and described.

* * * * *

MEIVOUFAL